(12) United States Patent
Ise et al.

(10) Patent No.: US 6,171,255 B1
(45) Date of Patent: Jan. 9, 2001

(54) DEVICE FOR NONINVASIVE BLOOD PRESSURE MEASUREMENT

(75) Inventors: Edgar Ise, Lübeck; Christoph Landowski, Stockelsdorf, both of (DE); Pieter W. J. M. Kemper, Waalre (NL)

(73) Assignee: Dräger Medizintechnik GmbH (DE)

( * ) Notice: Under 35 U.S.C. 154(b), the term of this patent shall be extended for 0 days.

(21) Appl. No.: 09/334,423

(22) Filed: Jun. 16, 1999

(30) Foreign Application Priority Data

Jan. 20, 1999 (DE) ............................................. 199 02 044

(51) Int. Cl.[7] .................................................. A61B 05/40
(52) U.S. Cl. ..................... 600/490; 4600/493; 4600/494
(58) Field of Search ........................... 600/490, 453–456, 600/500

(56) References Cited

U.S. PATENT DOCUMENTS

| | | | |
|---|---|---|---|
| 4,475,557 | * 10/1984 | Hatchek et al. | 600/493 |
| 4,987,900 | * 1/1991 | Eckerle et al. | 600/500 |
| 5,343,869 | 9/1994 | Pross et al. | |
| 5,568,814 | * 10/1996 | Gallant et al. | 600/493 |

FOREIGN PATENT DOCUMENTS 0 829 227 A2    3/1998  (EP) .

* cited by examiner

*Primary Examiner*—Robert L. Nasser
(74) *Attorney, Agent, or Firm*—McGlew and Tuttle, P.C.

(57) ABSTRACT

A pneumatic system of a device for noninvasive blood pressure measurement includes a pneumatic cuff which is connected to a multisensor block (9) by means of a pneumatic connection line (26). At least one sensor (13) sending electric output signals for measuring physiological parameters is connected to the multisensor block (9) by an electric connection line (23). The multisensor block (9) is connected to an evaluating and supply unit (8) by a single hybrid cable (10) containing a gas-carrying line (14) and at least two electric lines (15, 15').

18 Claims, 3 Drawing Sheets

DEVICE FOR NONINVASIVE BLOOD PRESSURE MEASUREMENT

FIELD OF THE INVENTION

The present invention pertains to a device for noninvasive blood pressure measurement including a pneumatic cuff wherein the pneumatic cuff is placed around an extremity of a patient and the pressure is determined by a device with a pressure gauge and the pressure is subsequently evaluated.

BACKGROUND OF THE INVENTION

Such a device has been known, e.g., from EP 0 829 227 A2. The pneumatic pressure in a cuff around an extremity of a patient is determined by means of such a device with a pressure gauge and subsequently evaluated. Important requirements imposed on such devices for practice include flexible handling, robustness and measurements not affected by external disturbances. External disturbances usually originate from mechanical effects on the pneumatic system of the measuring device, which comprises, in general, the elements cuff, pressure sensor, pump, valve, and pneumatic connection lines.

Mechanical effects on the pneumatic system, especially on the flexible pneumatic connection lines, are due, in particular, to movements of the patient and cause disturbing signals. However, these signals are not physiological and therefore lead to incorrect measurement results or even to an interruption of the measurement. It has therefore been suggested that such disturbances be compensated by numerical processes, but such processes are complicated and have ultimately no effect on the mechanical causes proper of the disturbances.

SUMMARY AND OBJECTS OF THE INVENTION

The primary object of the present invention is to provide an improved device for noninvasive blood pressure measurement, which extensively reduces the effect of external disturbances on the pneumatic system of the device.

According to the invention, a device for noninvasive blood pressure measurement is provided with a pneumatic cuff connected to a multisensor block means (i.e. a unit with a senor and a connection for another sensor)via a pneumatic connection line. At least one sensor is provided sending electric output signals for the measurement of physiological parameters. The sensor is connected to the multisensor block by means of an electric connection line. The multisensor block is connected to an evaluating and supply unit by means of a single hybrid cable containing a gas-carrying line and at least two electric lines.

The gas-carrying line and the electric lines, of which there are at least two, preferably form the hybrid cable with a common outer sheath, which is not elastic in the longitudinal direction. The gas-carrying line preferably covers the geometric center of the hybrid cable.

The gas-carrying line and the electric lines, of which there are at least two, may be twisted in the sheath with a twist cycle of 50 to 300 mm.

The sheath itself or a part of the sheath may consist essentially of a fiber-reinforced material or a composite, especially a synthetic fiber-reinforced composite, carbon fiber-reinforced composite or ceramic fiber-reinforced composite.

The multisensor block may be provided with a pneumatic plug-and-socket connection for the pneumatic connection line. The multisensor block may also be provided with an electric plug-and-socket connection for at least one electric connection line.

An important advantage of the present invention arises from the fact that a substantial improvement of the measurement results is achieved with simple design means in the area of the pneumatic system of the device. An important and advantageous feature of the present invention is a special hybrid cable, which contains a gas-carrying line and at least two electric lines and connects a multisensor block to an evaluating and supply unit.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
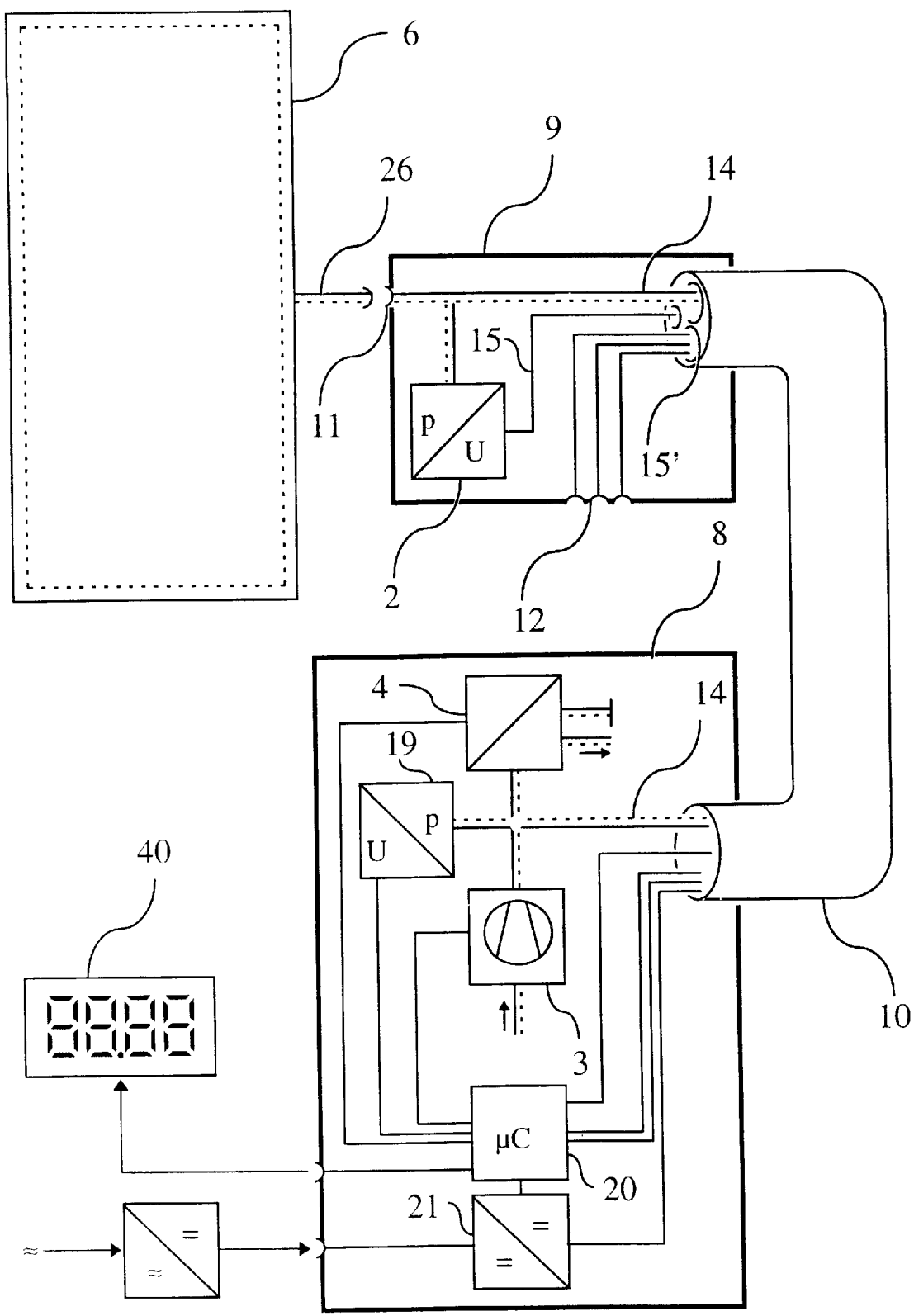
FIG. 1 is a schematic view showing a detailed representation of a device according to the present invention.

Referring to the drawings in particular, the principle of measurement of the noninvasive blood pressure measurement according to the invention is based on the interaction between the blood vessels of the extremities of a patient with a pneumatic system. In a pneumatic cuff 6, the pneumatic signal is coupled into the pneumatic system. Pneumatic lines transmit the pneumatic signal to a pressure sensor, which converts the pneumatic signal into an electric signal. The blood pressure of the patient is determined from the electric signal. Fluctuations in pressure, which are not physiological and may ultimately lead to errors in the measurement and evaluation, occur in the pneumatic system of the device according to the state of the art in the case of movement of the patient.

Figure 2:
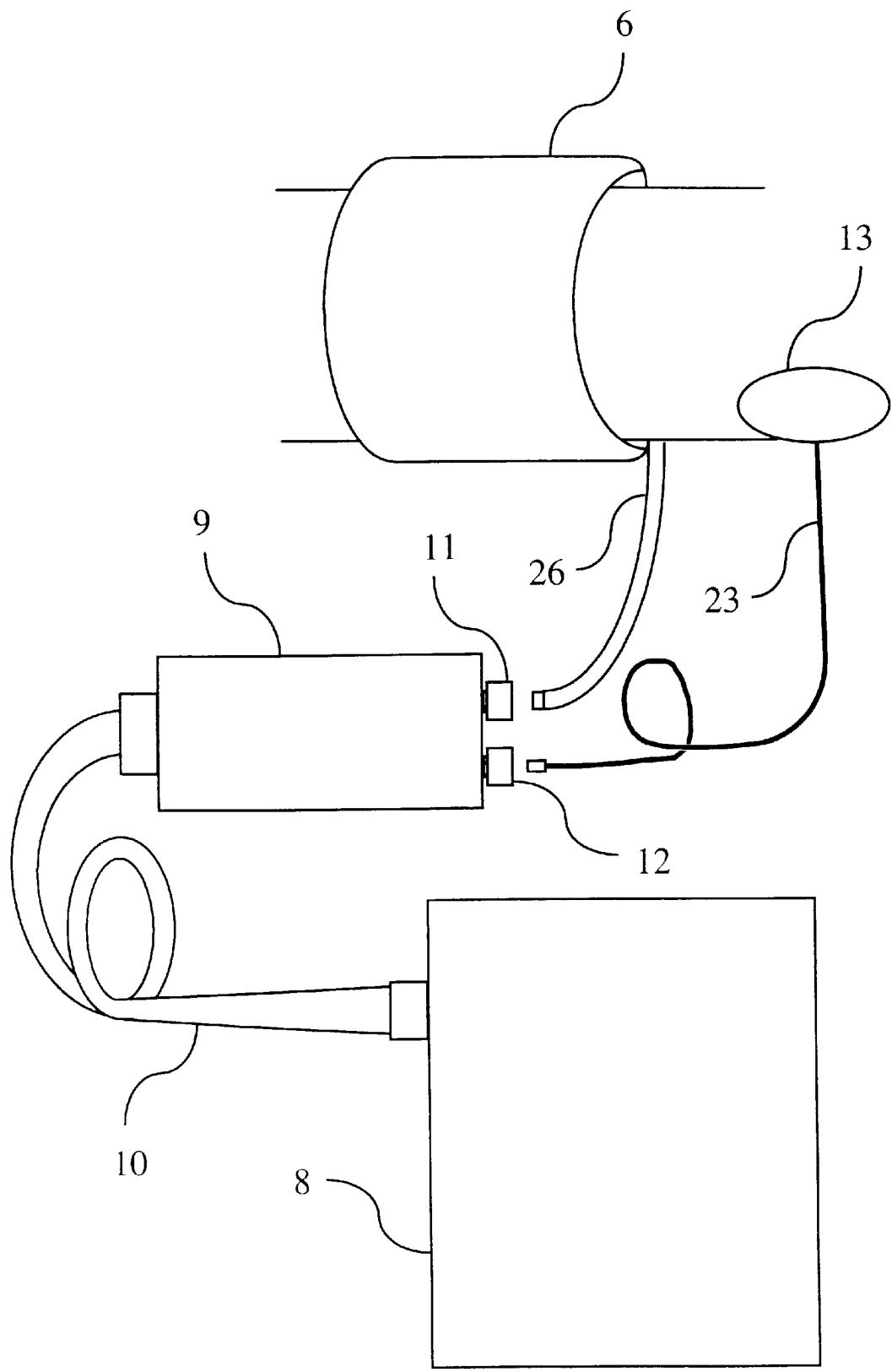
FIG. 2 is schematic perspective view showing essential elements of a device according to the present invention.

According to FIGS. 1 and 2, the device according to the present invention for noninvasive blood pressure measurement comprises three assembly units, namely, an evaluating and supply unit 8, a hybrid cable 10, and a multisensor block 9 (i.e. a sensor unit which preferably has a housing or enclosure). The pneumatic cuff 6 is connected to the multisensor block 9 via a pneumatic connection line 26, which is as short as possible, and via a coupling designed in the form of a pneumatic plug-and-socket connection 11.

A pump 3 is located in the evaluating and supply unit 8 in order to fill the pneumatic cuff 6 with air. The air flows over the gas-carrying line 14 of the hybrid cable 10 into the cuff 6. A control limits the pressure in the pneumatic system of the device. To achieve this, the static system pressure is measured with an overpressure sensor 19 and evaluated in a computing unit (e.g. a device with a microprocessor represented $\mu C$) 20 with respect to the operating state. The computing unit 20 opens a valve 4 to lower the system pressure and thus changes the operating state in the measuring cycle. A pressure sensor 2 with a high time and signal resolution measures the pneumatic system pressure. The measured value of the pneumatic system pressure is transmitted from the signal output (represented U) to the computing unit 20 in the evaluating and supply unit 8 via an electric line 15, which acts as a stabilizing/positioning element in the hybrid cable 10. The computing unit 20 displays the measured value in an external display 40. The electricity is supplied from a power supply unit and a d.c. power source 21.

The multisensor block 9 contains additional connections 12 for at least one sensor 13, whose electric line 15' is likewise embodied and acts as a stabilizing element or whose electric lines 15' are embodied and act as stabilizing elements in the hybrid cable 10 in the case of a plurality of sensors 13.

In the exemplary embodiment according to FIG. 1, electric plug-and-socket connections 12 are provided, e.g., for sensors 13 (FIG. 2) for the measurements of the heart action (electrocardiogram), body temperature and oxygen saturation.

The device according to FIG. 1 is schematically shown in FIG. 2 in a simplified representation, wherein the minimal configuration with a single sensor 13 for the measurement of physiological parameters is shown. The sensor 13 is connected to the multisensor block 9 by means of a corresponding electric connection line 23.

The components 8, 9, 10, 11 and 12 form a so-called terminal. The multisensor block 9 is part of such a terminal, it has a pneumatic plug-and-socket connection 11 for the pneumatic connection line 26 and at least one electric plug-and-socket connection 12 for at least one electric connection line 23. The multisensor block 9 has a permanent connection to the hybrid cable 10. The multisensor block 9 consequently separates electric and pneumatic lines.

Figure 3:
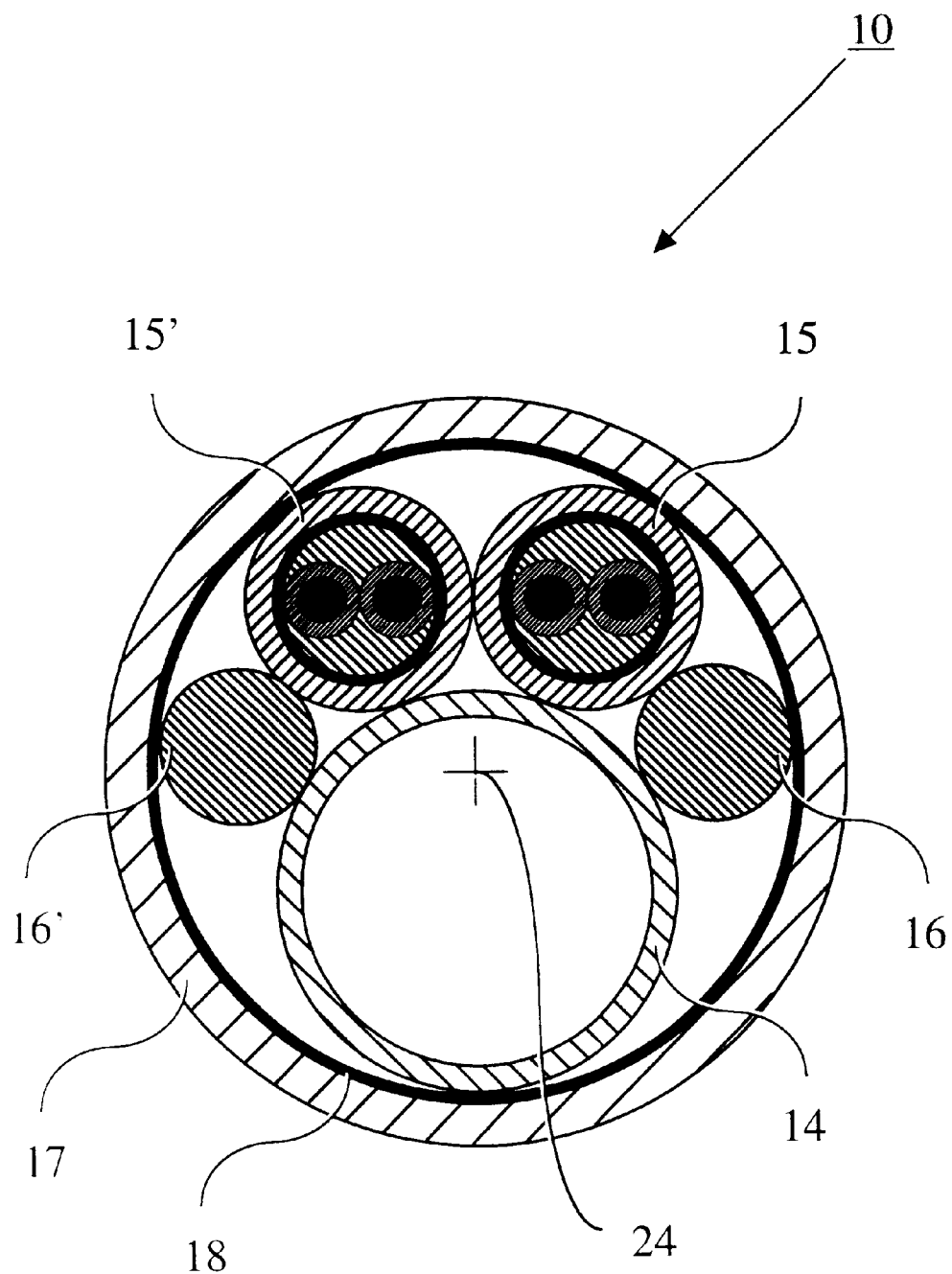
FIG. 3 is a cross sectional view through the hybrid cable of the device according to the present invention.

The hybrid cable 10 is explained by means of FIG. 3, which shows a cross section.

The hybrid cable 10 transmits both electric and pneumatic signals in one cable and has a substantially more stable behavior than a separate gas-carrying line 14. In the minimal configuration, a gas-carrying line 14 with an internal diameter of a few mm forms the hybrid cable 10 together with at least two electric lines 15, 15' with a common outer sheath, which is not elastic in the longitudinal direction, wherein the gas-carrying line 14 covers the geometric center 24 of the hybrid cable 10 and wherein the gas-carrying line 14 and the electric lines 15, 15', of which there are at least two, are twisted in the sheath 17 with a cycle of 50 to 300 mm.

The sheath 17 itself or at least part 18 of the sheath 17 preferably consists of a fiber-reinforced material or composite, especially a synthetic fiber-, carbon fiber- or ceramic fiber-reinforced composite.

FIG. 3 shows two optional position elements 16, 16', which position the cable assembly and are twisted with the other elements in the sheath 17.

The position elements 16, 16' may be arranged in the sheath 17 as polymeric strands or even as a uniformly distributed mass between the gas-carrying line 14 and the electric lines 15, 15', of which there are at least two. The sheath 17 or part 18 of the sheath 17 may consist of Gor-tex®.

While a specific embodiment of the invention has been shown and described in detail to illustrate the application of the principles of the invention, it will be understood that the invention may be embodied otherwise without departing from such principles.

What is claimed is:

1. A device for noninvasive blood pressure measurement, comprising:
   a pneumatic cuff;
   a multisensor block;
   a pneumatic connection line, said pneumatic cuff being connected to said multisensor block by said pneumatic connection line;
   a sensor sending electric output signals for the measurement of physiological parameters;
   an electric connection line, said sensor being connected to said multisensor block by means of an electric connection line;
   a single hybrid cable containing a gas-carrying line and at least two electric lines; and
   an evaluating and supply unit, said multisensor block being connected to said evaluating and supply unit by said single hybrid cable.

2. A device in accordance with claim 1, wherein said gas-carrying line and said at least two electric lines form said hybrid cable with a common outer sheath, which is not elastic in a longitudinal direction, wherein said gas-carrying line covers a geometric center of said hybrid cable.

3. The device in accordance with claim 2, wherein said gas-carrying line and said at least two electric lines, are twisted in said sheath with a twist cycle of from 50 to 300 mm.

4. The device in accordance with claim 2, wherein said sheath itself or a part of said sheath consists essentially of a fiber-reinforced material.

5. The device in accordance with claim 2, wherein said sheath itself or a part of said sheath consists essentially of a composite material.

6. The device in accordance with claim 5, wherein said sheath itself or a part of said sheath consists essentially of a synthetic fiber composite material.

7. The device in accordance with claim 5, wherein said sheath itself or a part of said sheath consists essentially of a carbon fiber composite material.

8. The device in accordance with claim 5, wherein said sheath itself or a part of said sheath consists essentially of a ceramic fiber-reinforced composite material.

9. The device in accordance with claim 1, wherein said multisensor block has a pneumatic plug-and-socket connection for said pneumatic connection line and an electric plug-and-socket connection for at least one of said electric connection line.

10. A blood pressure measurement system, comprising:
    a pneumatic cuff;
    a sensor unit including a housing;
    a pneumatic connection line, said pneumatic cuff being connected to said sensor unit by said pneumatic connection line;
    a sensor sending electric output signals for the measurement of physiological parameters;
    electric connection line, said sensor being connected to said sensor unit by means of an electric connection line;
    a single hybrid cable containing a gas-carrying line and at least two electric lines; and
    an evaluating and supply unit, said sensor unit being connected to said evaluating and supply unit by said single hybrid cable.

11. The system in accordance with claim 10, wherein said gas-carrying line and said at least two electric lines form said hybrid cable with a common outer sheath, which is not elastic in a longitudinal direction, wherein said gas-carrying line covers a geometric center of said hybrid cable.

12. The system in accordance with claim 11, wherein said gas-carrying line and said at least two electric lines, are twisted in said sheath with a twist cycle of from 50 to 300 mm.

13. The system in accordance with claim 11, wherein said sheath itself or a part of said sheath consists essentially of a fiber-reinforced material.

14. The system in accordance with claim 11, wherein said sheath itself or a part of said sheath consists essentially of a composite material.

15. The system in accordance with claim 14, wherein said sheath itself or a part of said sheath consists essentially of a synthetic fiber composite material.

16. The system in accordance with claim 14, wherein said sheath itself or a part of said sheath consists essentially of a carbon fiber composite material.

17. The system in accordance with claim 14, wherein said sheath itself or a part of said sheath consists essentially of a ceramic fiber-reinforced composite material.

18. The system in accordance with claim 10, wherein said multisensor block has a pneumatic plug-and-socket connection for said pneumatic connection line and an electric plug-and-socket connection for at least one of said electric connection line.

* * * * *